United States Patent
Hase et al.

(10) Patent No.: US 9,695,107 B2
(45) Date of Patent: Jul. 4, 2017

(54) CURABLE SENSITIZER, PHOTOCURABLE MATERIAL, CURED PRODUCT, AND MATERIAL FOR WIRING HARNESS

(71) Applicants: AUTONETWORKS TECHNOLOGIES, LTD., Yokkaichi-shi, Mie (JP); SUMITOMO WIRING SYSTEMS, LTD., Yokkaichi-shi, Mie (JP); SUMITOMO ELECTRIC INDUSTRIES, LTD., Osaka-shi, Osaka (JP); KYUSHU UNIVERSITY, Fukuoka-shi, Fukuoka (JP)

(72) Inventors: Tatsuya Hase, Yokkaichi (JP); Makoto Mizoguchi, Fukuoka (JP)

(73) Assignees: SUMITOMO WIRING SYSTEMS, LTD., Mie (JP); SUMITOMO ELECTRIC INDUSTRIES, LTD., Osaka (JP); KYUSHU UNIVERSITY, Fukuoka (JP); AUTONETWORKS TECHNOLOGIES, LTD., Mie (JP)

( * ) Notice: Subject to any disclaimer, the term of this patent is extended or adjusted under 35 U.S.C. 154(b) by 0 days.

(21) Appl. No.: 14/401,737

(22) PCT Filed: May 22, 2013

(86) PCT No.: PCT/JP2013/064164
§ 371 (c)(1),
(2) Date: Nov. 17, 2014

(87) PCT Pub. No.: WO2013/183446
PCT Pub. Date: Dec. 12, 2013

(65) Prior Publication Data
US 2015/0166458 A1  Jun. 18, 2015

(30) Foreign Application Priority Data
Jun. 7, 2012 (JP) ................................. 2012-129492

(51) Int. Cl.
C08F 2/46 (2006.01)
C08F 120/26 (2006.01)
C07C 69/54 (2006.01)
C08F 2/50 (2006.01)
C07C 67/08 (2006.01)
C07C 69/602 (2006.01)
C08F 22/10 (2006.01)
C08F 22/20 (2006.01)

(52) U.S. Cl.
CPC .............. C07C 69/54 (2013.01); C07C 67/08 (2013.01); C07C 69/602 (2013.01); C08F 2/50 (2013.01); C08F 22/105 (2013.01); C08F 22/20 (2013.01)

(58) Field of Classification Search
CPC .............. C08F 2/46; C08F 2/48; C08F 120/26

USPC ....................................................... 526/320
See application file for complete search history.

(56) References Cited

U.S. PATENT DOCUMENTS

| | | | |
|---|---|---|---|
| 5,336,574 A | 8/1994 | Igarashi et al. | |
| 5,393,800 A * | 2/1995 | Grosclaude | C09J 4/00 522/170 |
| 5,597,388 A | 1/1997 | Fritzsche | |
| 5,703,139 A * | 12/1997 | Kim | C08F 22/105 522/174 |
| 6,583,195 B2 * | 6/2003 | Sokol | C09D 4/00 522/103 |
| 6,590,070 B1 | 7/2003 | Toriumi et al. | |
| 6,797,740 B2 * | 9/2004 | Abel | C03C 25/1065 385/114 |
| 7,495,034 B2 * | 2/2009 | Litke | A61F 11/08 522/113 |
| 8,362,102 B2 * | 1/2013 | Jeremic | C09D 11/101 427/256 |
| 8,362,357 B2 * | 1/2013 | Nesbitt | C09D 175/16 136/251 |

(Continued)

FOREIGN PATENT DOCUMENTS

| | | |
|---|---|---|
| CN | 102050930 A | 5/2011 |
| JP | A-7-507112 | 8/1995 |
| JP | A-2001-64593 | 3/2001 |
| JP | 2001-107009 A | 4/2001 |
| JP | A-2005-40749 | 2/2005 |
| JP | A-2005-163010 | 6/2005 |
| JP | A-2007-161998 | 6/2007 |
| JP | A-2008-169234 | 7/2008 |
| JP | 2011-520561 A | 7/2011 |
| JP | A-2012-107198 | 6/2012 |

(Continued)

OTHER PUBLICATIONS

Machine translation of CN1914771A.*

(Continued)

*Primary Examiner* — Vu A Nguyen
(74) *Attorney, Agent, or Firm* — Oliff PLC

(57) ABSTRACT

A curable sensitizer that exhibits a radical-polymerization sensitizing ability that conventional sensitizers do not have in a polymerization reaction using radicals, and is easily available at a low cost, a photocurable material containing the sensitizer, a cured product of the photocurable material, and a material for a wiring harness containing the photocurable material. The curable sensitizer contains an alcohol (meth)acrylate synthesized from an alcohol having one or more hydroxy groups and two or more oxygen atoms in a molecule and a (meth) acrylate ingredient selected from a (meth)acrylic acid and a derivative thereof. An ester bond is formed between one of the hydroxy groups of the alcohol and the (meth)acrylate ingredient. The sensitizer is capable of increasing curability of a curable material when mixed in the material. The photocurable material contains the curable sensitizer and a photoinitiator. The material for the wiring harness contains the photocurable material.

9 Claims, No Drawings

(56) References Cited

U.S. PATENT DOCUMENTS

| | | | |
|---|---|---|---|
| 2004/0132862 A1* | 7/2004 | Woudenberg | C09D 11/34 523/160 |
| 2005/0023665 A1 | 2/2005 | Ledwidge | |
| 2008/0258345 A1* | 10/2008 | Bens | C08F 290/06 264/401 |
| 2009/0173438 A1 | 7/2009 | Takeuchi et al. | |
| 2009/0287306 A1 | 11/2009 | Smith et al. | |
| 2011/0254790 A1 | 10/2011 | Suzuki et al. | |
| 2012/0016079 A1* | 1/2012 | Weiskopf | C07C 68/02 524/770 |
| 2013/0062114 A1* | 3/2013 | Inoue | C09D 4/00 174/72 A |

FOREIGN PATENT DOCUMENTS

| | | |
|---|---|---|
| WO | WO 93/24701 A1 | 12/1993 |
| WO | 98/33761 A1 | 8/1998 |
| WO | 02/14326 A1 | 2/2002 |
| WO | 03/066687 A2 | 8/2003 |
| WO | 2005/071792 A1 | 8/2005 |

OTHER PUBLICATIONS

International Search Report issued in International Patent Application No. PCT/JP2013/064164 dated Sep. 3, 2013.
Aug. 4, 2015 Office Action issued in Chinese Patent Application No. 201380029308.2.
Sep. 15, 2015 Office Action Issued in Japanese Patent Application No. 2012-129492.
Sep. 15, 2015 Office Action issued in Korean Patent Application No. 10-2014-7035555.
Mar. 8, 2016 Office Action issued in Chinese Patent Application No. 201380029308.2.
Feb. 11, 2016 Supplementary European Search Report issued in European Application No. 13800910.5.
Apr. 19, 2016 Office Action issued in Japanese Patent Application No. 2012-129492.
Mar. 23, 2016 Korean Office Action issued in Korean Patent Application No. 10-2014-7035555.
Mar. 10, 2017 Office Action issued in Chinese Patent Application No. 201380029308.2.
Aug. 29, 2016 Office Action issued in Chinese Patent Application No. 201380029308.2.

* cited by examiner

CURABLE SENSITIZER, PHOTOCURABLE MATERIAL, CURED PRODUCT, AND MATERIAL FOR WIRING HARNESS

TECHNICAL FIELD

The present invention relates to a curable sensitizer, a photocurable material containing the sensitizer, a cured product of the photocurable material, and a material for a wiring harness containing the photocurable material.

BACKGROUND ART

Polymerization reactions are important in forming various kinds of materials. Among the reactions, a radical polymerization reaction is widely used because the reaction proceeds fast and because various raw materials may be used in the reaction.

To be specific, in the radical polymerization reaction, a compound that generates radicals is added into a monomer or oligomer having a double bond such as an acrylate derivative, and a polymerization reaction is initiated and promoted. In many cases, the reaction proceeds so fast that heating for a long time is not required.

The fastness of the reaction is due to high reactivity of the radicals. On the other hand, the radicals have very short lives, and are easily deactivated by a deactivator such as oxygen. Thus, the reaction does not occur outside the region where the free radicals are generated.

Further, if the generated radicals are spatially inhomogeneous in amount, polymerized material is accordingly inhomogeneous in molecular weight, so that a highly reliable material cannot be obtained.

Especially, when a photocurable material containing a photoinitiator is radically polymerized by irradiation of light from the surface thereof and by consequent radical generation in order to provide a cured product having a certain thickness or larger, a deep portion of the material that the light is hard to reach is not sufficiently cured.

Thus, in order to cure the material with more sufficient homogeneity, larger amount of radicals are required to be generated. However, long-time photoirradiation and long-time heating are necessary to generate a large amount of radicals. The properties of the cured product may rather be deteriorated by the long-time irradiation and heating.

Further, if a method is provided by which a sufficiently cured product can be produced with less energies even in a portion that is easily irradiated with the light, the method is ideal from the viewpoint of workability and energy consumption.

In order to solve the problem described above, various kinds of sensitizers as additives have been studied (see Patent Literatures 1-4).

CITATION LIST

Patent Literature

Patent Literature 1: JP 2001-064593 A
Patent Literature 2: JP 2007-161998 A
Patent Literature 3: JP 2005-040749 A
Patent Literature 4: JP 2005-163010 A

SUMMARY OF INVENTION

Technical Problem

In the methods described in Patent Literatures 1 and 2, some kinds of amine compounds are used as additives. Addition of the amine compounds imparts basicity to photocurable materials, and thus increases reactivity of double bonds in photoinitiators and (meth)acrylates.

In the methods described in Patent Literature 3 and 4, anthracene derivatives and chitosan derivatives, which have high molar absorbance coefficients in wide wavelength ranges, are mixed in photocurable materials. The additives release high excitation energies when irradiated with light.

However, though increasing reactivities of the photocurable materials, the methods described in Patent Literatures 1-4 decreases the storage stabilities of the materials. Thus, curing reactions gradually proceed in the mixtures of the materials and the additives even when the mixtures are stored in cool and dark places.

Further, in the methods described in Patent Literatures 1 and 2, colors of the photocrosslinking materials may be changed by the amines. In the methods described in Patent Literatures 3 and 4, the additives have small solubilities.

An object of the present invention is to provide a curable sensitizer that exhibits a radical-polymerization sensitizing ability that conventional sensitizers do not have in a polymerization reaction using radicals, and is easily available at a low cost, and to provide a photocurable material containing the sensitizer, a cured product of the photocurable material, and a material for a wiring harness containing the photocurable material.

Solution to Problem

To achieve the objects and in accordance with the purpose of the present invention, a curable sensitizer according to a preferred embodiment of the present invention contains an alcohol (meth)acrylate synthesized from an alcohol having one or more hydroxy groups and two or more oxygen atoms in a molecule and a (meth)acrylate ingredient selected from a (meth)acrylic acid and a derivative thereof, an ester bond formed between one of the hydroxy groups of the alcohol and the (meth)acrylate ingredient, the sensitizer being capable of increasing curability of a curable material when mixed in the material.

In another aspect of the present invention, a photocurable material according to a preferred embodiment of the present invention contains, at least, the curable sensitizer described above and a photoinitiator.

In another aspect of the present invention, a cured product according to a preferred embodiment of the present invention is a cured product of the photocurable material described above.

In another aspect of the present invention, a material for a wiring harness according to a preferred embodiment of the present invention contains the photocurable material described above.

Advantageous Effects of Invention

The curable sensitizer according the preferred embodiment of the present invention contains the alcohol (meth) acrylate synthesized from the alcohol having the one or more hydroxy groups and the two or more oxygen atoms in the molecule and the (meth)acrylate ingredient. The ester bond is formed between the one of the hydroxy group of the alcohol and the (meth)acrylate ingredient. The sensitizer is capable of increasing curability of the curable material when mixed in the material. Thus, the sensitizer exhibits a radical-polymerization sensitizing ability that conventional sensitizers do not have in a polymerization reaction using radicals. Further, the curable sensitizer is available at a low cost.

Further, the curable sensitizer has less possibility of causing a problem of changing colors of the material or a problem due to a low solubility than the conventional sensitizers. Thus, the curable sensitizer is easily used to be added into various kinds of curable materials.

DESCRIPTION OF EMBODIMENTS

A detailed description of a preferred embodiment of the present invention will now be provided. According to investigations by the present inventors, an alcohol (meth)acrylate synthesized from an alcohol having one or more hydroxy groups and two or more oxygen atoms in a molecule and a (meth)acrylate ingredient by formation of an ester bond between one of the hydroxy groups of the alcohol and the (meth)acrylic ingredient works as a curable sensitizer that sensitizes a curing reaction using radical polymerization when the sensitizer is mixed in a curable material such as a photocurable resin. It is to be noted that the term "(meth) acrylate" refers to both a methacrylate and an acrylate in the present invention.

According to a presumable mechanism for the sensitizing of the curing reaction, active species such as hydroxy radicals and ketyl radicals are generated during activation and polymerization of the (meth)acrylate groups in the curable sensitizer by radicals generated by a radical source such as a photoinitiator. Then, the generated activated species activates an unreacted portion of the photoinitiator, and thus generates new radicals.

The curable sensitizer is cured finally, even alone, and thus does not remain in the material in a form of an uncured compound. If the cured product of the sensitizer has adequate properties, the photocurable material may contain only the curable sensitizer and an appropriate photoinitiator.

The curable sensitizer may also be used as an additive that is added into a radical-polymerizable curable material such as a conventional photocurable material in order to increase the polymerization reactivity of the material.

The curable material into which the curing sensitizer is added is not limited specifically as long as the material is cured by a radical polymerization reaction; however, a photocurable material is preferably used. By addition of the curable sensitizer into the photocurable material, a highly sensitive photocurable material is provided in which the polymerization reaction proceeds with a high sensitivity even in a portion where only a small amount of radicals are generated.

In the curable sensitizer, one of the hydroxy groups of the alcohol having the one or more hydroxy groups and the two or more oxygen atoms in the molecule forms the ester bond with the (meth)acrylate ingredient. The double bond in the (meth)acrylate is activated by radicals generated from a radical source such as a photoinitiator, first. Then, a part of the energy generated by the activation was consumed in release of the alcohol moiety, whereby hydroxy radicals and ketyl radicals are newly generated. The release of the alcohol moiety particularly tends to be initiated by extraction of a hydrogen atom at an a position of an ether bond.

Since the radicals have energies that can activate the photoinitiator, the radicals work as a new activation source replacing the light. Thus, the radicals activate the uncured photoinitiator in a portion that is not sufficiently activated by the light. Repeated cycles of this reaction work as a multiplying mechanism.

To be specific, the curable sensitizer works, while coexisting with the photoinitiator, as a core material in a cycle in which the radical species that the sensitizer received at an early stage of the reaction are multiplied.

Accordingly, when the sensitizer is added into a reactant to be subjected to radical polymerization, such as a photocurable material, a curing reaction of the reactant proceeds with a higher sensitivity. Thus, a cured product having a shape that cannot be cured in the case of conventional methods can be obtained.

Further, the curable material containing the curable sensitizer can be stored for a long time in a condition where the material is not irradiated with light because the above-described multiplying cycle is not initiated without photoirradiation.

The content of the curable sensitizer in the photocurable material is preferably 1 mass % or higher with respect to the total amount of the ingredients of the material including the curable sensitizer and the photoinitiator, from the viewpoint of providing a sufficient sensitizing ability. When the content is too low, the sensitizer may not work sufficiently to provide an adequate sensitizing ability.

On the other hand, the content of the curable sensitizer is preferably 95 mass % or lower with respect to the total amount of the ingredients of the material including the curable sensitizer and the photoinitiator, from the view point of easiness in impartment and adjustment of an intended property of the material such as softness.

Examples of the alcohol having the one or more hydroxy groups and the two or more oxygen atoms in the molecule that forms the curable sensitizer include a monovalent alcohol and a multivalent alcohol (i.e., a polyol), which denotes a divalent or higher-valent alcohol.

Specific examples of the alcohol include a dialcohol that has hydroxy groups at both terminal ends and has a chain of 1-30 carbon atoms; an alcohol that has a hydroxy group at one of the terminal ends and has one or more ether bonds; and diol-terminated poly(ethylene glycol), poly(propylene glycol), poly(tetramethylene glycol), poly(hexamethylene glycol), polycaprolactone, polyester polyol, polyamide, and polyester.

According to the principle of the sensitizing of the curing reaction, the double bond in the (meth)acrylate of the sensitizer is activated by radicals generated from a radical source such as the photoinitiator. Then, a part of the energy generated by the activation was consumed in release of the polyol moiety, and hydroxy radicals and ketyl radicals are newly generated. The newly generated radicals activate the unreacted portion of the photoinitiator. The release of the polyol moiety particularly tends to be initiated by extraction of a hydrogen atom at an a position of an ether bond.

Therefore, it is preferable that one or more of the oxygen atoms of the alcohol having the one or more hydroxy groups and the two or more oxygen atoms in the molecule form ether bonds.

Examples of the (meth)acrylate ingredient that forms the ester bond with the hydroxy group of the alcohol include (meth)acrylic acid and a derivative thereof. Examples of the derivative include a (meth)acrylate ester, a (meth)acrylic acid halogenate, and (meth)acrylic anhydride.

Specific examples of the alcohol (meth)acrylate synthesized from the alcohol having the one or more hydroxy groups and the two or more oxygen atoms in the molecule and the (meth)acrylate ingredient by formation of the ester bond between the one of the hydroxy groups of the alcohol and the (meth)acrylic ingredient include hydroxyethyl (meth)acrylate, hydroxypropyl (meth)acrylate, hydroxybutyl (meth)acrylate, tetrahydrofurfuryl (meth)acrylate, poly (ethylene glycol) mono(meth)acrylate, poly(propylene glycol) mono(meth)acrylate, methoxyethylene glycol (meth) acrylate, ethoxyethyl (meth)acrylate, methoxypolyethylene glycol (meth)acrylate, methoxypolypropylene glycol (meth) acrylate, polyoxyethylene nonyl phenyl ether acrylate, butanediol di(meth)acrylate, hexanediol di(meth)acrylate, nonanediol di(meth)acrylate, decanediol di(meth)acrylate, 2-butyl-2-ethyl-1,3-propanediol di(meth)acrylate, 2-hydroxy-3-acryloyloxy propyl methacrylate, dipropylene glycol di(meth)acrylate, tripropylene glycol di(meth)acrylate, triethylene glycol di(meth)acrylate, tetraethylene glycol di(meth)acrylate, tricyclodecane dimethylol di(meth)acrylate, 1,4-butanepolyol di(meth)acrylate, 1,6-hexanepolyol di(meth)acrylate, neopentyl glycol di(meth)acrylate, polyethylene glycol di(meth)acrylate, polypropylene glycol di(meth)acrylate, 9,9-bis[4-(2-acryloyloxyethoxy)phenyl] fluorene, polyester di(meth)acrylate, tris(2-hydroxyethyl) isocyanurate tri(meth)acrylate, tris-(2-hydroxyethyl) isocyanurate di(meth)acrylate, tricyclodecane dimethylol di(meth) acrylate, di(meth)acrylate of ethylene oxide (EO) modified bisphenol A, di(meth)acrylate of EO or propylene oxide (PO) modified hydrogenated bisphenol A, an epoxy (meth) acrylate obtained by addition of a (meth)acrylate to diglycidyl ether of bisphenol A, triethylene glycol divinyl ether, trimethylolpropane tri(meth)acrylate, pentaerythritol tri (meth)acrylate, tri(meth)acrylate of EO modified trimethylolpropane, tris-acryloyloxyethyl phosphate, pentaerythritol tetra(meth)acrylate, tetrafurfuryl alcohol oligo(meth)acrylate, ethyl carbitol oligo(meth)acrylate, 1,4-butanediol oligo (meth)acrylate, 1,6-hexanediol oligo(meth)acrylate, trimethylolpropane oligo(meth)acrylate, and pentaerythritol oligo(meth)acrylate. They may be used singly or in combination.

Specific examples of the photoinitiator (i.e., a photopolymerization initiator) include 1-hydroxycyclohexyl phenyl ketone, 2,2-dimethoxy-2-phenylacetophenone, xanthone, fluorenone, benzaldehyde, fluorene, anthraquinone, ethylanthraquinone, triphenylamine, carbazole, 3-methylacetophenone, 4-chlorobenzophenone, 4,4'-dimethoxybenzophenone, 4,4'-diaminobenzophenone, Michler's ketone, benzoin propyl ether, benzoin ethyl ether, benzil dimethylketal, 1-(4-isopropylphenyl)-2-hydroxy-2-methylpropane-1-one, 2-hydroxy-2-methyl-1-phenylpropane-1-one, thioxanthone, diethylthioxanthone, 2-isopropylthioxanthone, 2-chlorothioxanthone, 2-methyl-1-[4-(methylthio)phenyl]-2-morpholino-pr opane-1-one, 2,4,6-trimethyl benzoyl diphenyl phosphine oxide, and bis-(2,6-dimethoxy benzoyl)-2,4,4-trimethylpentyl phosphine oxide. They may be used singly or in combination.

Examples of commercial products that may be used as the photoinitiator include IRGACUREs 184, 369, 651, 500, 907, CGI1700, CGI1750, CGI1850, and CG24-61; DAROCUREs 1116 and 1173; LucirinTPO (all manufactured by BASF); and EBECRYL P36 (manufactured by UCB).

A conventional photocurable material may be used as the photocurable material described above. Specifically, a material that have a basic composition containing a curable monomer or oligomer such as a (meth)acrylate and a photoinitiator and may be cured by photoirradiation may be used.

According to the principle of curing of a photocurable material, a photoinitiator absorbs the irradiation light, and thereby generates activated species such as radical species. Then, the activated species radically polymerize carbon-carbon double bonds in ingredients such as the (meth) acrylate, and cures the material. However, in conventional photocurable materials, deep portions or portions that the light does not reach are not sufficiently cured when, for example, the materials have shapes having certain thicknesses or larger.

Meanwhile, when the curable sensitizer according to the preferred embodiment of the present invention is added into the photocurable material, the sensitizer works as a new activation source replacing the light, and activates the unreacted portion of the photoinitiator that is not activated sufficiently by the light. Repeated cycles of this reaction work as a multiplying mechanism. Thus, the curing reaction proceeds with a high sensitivity, and a cured product having a shape that cannot be cured in the case of conventional methods can be obtained.

Further, since the multiplying cycle is not initiated without photoirradiation, the photocurable material may be stored stably for a long time.

The curable sensitizer and the photocurable material may further contain various kinds of additives as necessary within a range of not impairing the object of the present invention. Examples of the additives include a stabilizer, a pigment, a dye, an antistatic agent, a flame retardant, a solvent, an antibacterial agent, and a fungicide.

Examples of the stabilizer include an antiaging agent, an antioxidant, and a dehydrating agent. Specific examples of the stabilizer include a hindered phenol compound, a hindered amine compound (antiaging agents); butylhydroxytoluene, butylhydroxyanisole, triphenyl phosphite (antioxidants); maleic anhydride, phthalic anhydride, benzophenonetetracarboxylic dianhydride, calcined lime, a carbodiimide derivative, and an acid chloride such as stearic acid chloride (dehydrating agents). A small amount of polymerization inhibitor such as methoquinone may also be used as the stabilizer.

It is to be noted that most of the stabilizers described above have negative influences on the radical chain reaction, so that it is preferable that the stabilizers are added to the material only in a small amount.

Examples of the pigment include an inorganic pigment such as titanium dioxide, zinc oxide, ultramarine, colcothar, lithopone, lead, cadmium, iron, cobalt, aluminum, a hydrochloride, and a sulfate; and an organic pigment such as an azo pigment and a copper phthalocyanine pigment.

Examples of the antistatic agent include a hydrophilic compound such as a quaternary ammonium salt, a polyglycol, and an ethylene oxide derivative.

Examples of the flame retardant include a chloroalkyl phosphate, dimethyl/methyl phosphonate, a bromine/phosphorous compound, an ammonium polyphosphate, a neopentylbromide-polyether, and a brominated polyether.

Examples of the solvent include any solvent as long as the solvent dissolves the sensitizer to reduce the viscosity of the sensitizer, or to increase the compatibility of the sensitizer. Specific examples of the solvent include a polar solvent such as tetrahydrofuran, dimethylformamide, ethyl acetate, and methyl ethyl ketone, and a chlorine-containing solvent such as dichloroethane and trichlorobenzene.

The additives may be used in combination, as appropriate. The method for mixing the additives in the sensitizer or in the photocurable material is not limited specifically; however, it is preferable that the additives are sufficiently agitated or blended with the sensitizer or the material to be dissolved or uniformly dispersed, with the use of an agitation equipment such as a blender, under a reduced pressure or in an inert gas atmosphere such as a nitrogen atmosphere.

The method for adding the curable sensitizer into the photocurable material is not limited specifically, either; however, it is preferable that the sensitizer is sufficiently agitated or blended with the material to be dissolved or uniformly dispersed, with the use of an agitation equipment such as a blender, at an appropriate temperature, under a reduced pressure or in an inert gas atmosphere such as a nitrogen atmosphere.

A cured product according to a preferred embodiment of the present invention is produced by polymerization and consequent curing of the above-described photocurable material containing the curable sensitizer and the photoinitiator through generation of radicals such as by photoirradiation. The photocurable material may contain a radical-polymerizable material, as described above.

Visible light may also be used to irradiate the photocurable material for providing the cured product, as well as the ultraviolet light. A variety of conventionally known irradiation devices may be used for the ultraviolet irradiation. Conditions for the ultraviolet irradiation may be determined as appropriate in accordance with the composition of the photocurable material.

A material for a wiring harness according to a preferred embodiment of the present invention contains the photocurable material described above. The material for the wiring harness may be contained in various kinds of components that constitute a wiring harness A wiring harness contains a single coated wire or a plurality of coated wires collected together, and the wire(s) are connected to connection terminal(s) at the terminal(s) thereof. The wire(s) in the wiring harness may be covered with a material such as a protection material. Specific examples of the component of the wiring harness that contains the material for the wiring harness include a wire coating, a connector, a molded object, and an adhesive. The material for the wiring harness is molded into a given shape by an appropriate molding method in accordance with the type of the component, and then the curable material in the material for the wiring harness is cured by irradiation of the molded product with light such as ultraviolet.

EXAMPLE

A description of the present invention will now be specifically provided with reference to examples; however, the present invention is not limited to the examples.

Table 1 shows Preparation Examples of photocurable materials. The ingredients shown in Table 1 are mixed and dispersed or dissolved in the content ratios (in part by mass) shown in the table with the use of an agitation equipment. Thus, the ultraviolet curable materials according to Preparation Examples shown in the table are prepared.

Tables 2 and 3 show Examples and Comparative Examples, respectively. The ingredients shown in Tables 2 and 3 are mixed and dispersed or dissolved in the content ratios (in part by mass) shown in the tables with the use of an agitation equipment. Thus, the compositions according to Examples and Comparative Examples shown in the tables are prepared.

Abbreviations described below are used in Tables 1-3. Reagents with no specific indication of manufacturer are reagent-grade products manufactured by TOKYO CHEMICAL INDUSTRY CO., LTD.

[(Meth)acrylates]
  IBA: isobornyl acrylate
  STMA: stearyl methacrylate
[Photoinitiators (Ultraviolet Initiators)]
  HCHPK: 1-hydroxycyclohexyl phenyl ketone
  HMPPO:
  2-hydroxy-2-methyl-1-phenylpropane-1-one (manuf.: BASF; trade name: DAROCUR1173)

[Sensitizers]
  HPA: hydroxypropyl acrylate
  DPGA: dipropylene glycol diacrylate
  TEGA: tetraethylene glycol diacrylate
  HAPMA: 2-hydroxy-3-acryloyloxy propyl methacrylate
  BAEDA: diacrylate of ethylene oxide modified bisphenol A (manuf.: SHIN-NAKAMURA CHEMICAL CO., LTD)
  TMPETA: triacrylate of ethylene oxide modified trimethylolpropane (manuf.: OSAKAORGANIC CHEMICAL INDUSTRY LTD.)

[Evaluation Method for Length of Cured Product in Deep Portion]

Each of the compositions shown in Tables 2 and 3 was put in a hard Teflon tube that has an inner diameter of 10 mm and has a Teflon stopper filling the opening at the bottom of the tube. The liquid level of the composition was set 50 mm high. Then the composition was irradiated with ultraviolet for 2 seconds on the upper surface thereof with the use of a UV lamp (100 mW/cm$^2$, manufactured by SEN LIGHTS CO., LTD.). If a radical polymerization was caused by the irradiation, the composition solidified. Thus, when the Teflon stopper at the bottom of the tube was removed after the irradiation, a liquid portion of the composition that did not undergo the radical polymerization reaction flowed out of the tube while a solid portion (i.e., radical polymerized product) remained in the tube. Thus, a longer solid portion that remained in the tube indicates that the radical polymerization reaction proceeded in a deeper portion that the light is harder to reach, and that a certain amount of energy of the irradiation light caused the curing reaction more effectively. Accordingly, the lengths of the remaining solid portions in the Teflon tube after the photoirradiation are shown at the bottoms of Tables 2 and 3 as lengths of remaining cured products to represent the curability of the compositions.

Evaluation Results

Examples 1-10 and Comparative Examples 1-3

The compositions according to the Comparative Example 1-3 do not contain a sensitizer. Thus, the curing reaction did not proceed sufficiently in deep portions of the compositions. This result indicates that the energy of the light used for the irradiation did not cause the radical polymerization reaction sufficiently. Meanwhile, compositions according to Examples 1-10 contain sensitizers. The remaining cured products of the compositions had larger lengths than those of Comparative Examples 1-3. Thus, in the compositions according to Examples 1-10, curing by the radical polymerization reaction was achieved in deep portions that were hard to be reached by light and thus were impossible to be cured in the case of the conventional photocurable materials. Therefore, it was confirmed that sensitivities of the photocurable materials according to Examples 1-10 were increased. This result indicates that the photocurable materials according to Examples 1-10 can be cured into complicated or thick shapes.

TABLE 1

| | | Preparation Example | | |
| --- | --- | --- | --- | --- |
| | | A-1 | A-2 | A-3 |
| (Meth)acrylate | IBA | 100 | | 100 |
| | STMA | | 100 | |
| Photoinitiator | HCHPK | 2 | 2 | |
| | HMPPO | | | 2 |

TABLE 2

|  |  | Example | | | | | | | | | |
|---|---|---|---|---|---|---|---|---|---|---|---|
|  |  | 1 | 2 | 3 | 4 | 5 | 6 | 7 | 8 | 9 | 10 |
| Ultraviolet Curable Material | A-1 | 80 | 80 | 80 | 80 | 80 | 80 |  |  | 10 | 99 |
|  | A-2 |  |  |  |  |  |  | 80 |  |  |  |
|  | A-3 |  |  |  |  |  |  |  | 80 |  |  |
| Sensitizer | HPA | 20 |  |  |  |  |  |  |  |  |  |
|  | DPGA |  | 20 |  |  |  |  | 20 | 20 | 90 | 1 |
|  | TEGA |  |  | 20 |  |  |  |  |  |  |  |
|  | HAPMA |  |  |  | 20 |  |  |  |  |  |  |
|  | BAEDA |  |  |  |  | 20 |  |  |  |  |  |
|  | TMPETA |  |  |  |  |  | 20 |  |  |  |  |
| Length of Remaining Cured Product [mm] |  | 5.6 | 7.6 | 6.8 | 5.7 | 6.7 | 7.9 | 6.9 | 7.2 | 7.3 | 3.9 |

TABLE 3

|  |  | Comparative Example | | |
|---|---|---|---|---|
|  |  | 1 | 2 | 3 |
| Ultraviolet Curable Material | A-1 | 100 |  |  |
|  | A-2 |  | 100 |  |
|  | A-3 |  |  | 100 |
| Sensitizer | HPA |  |  |  |
|  | DPGA |  |  |  |
|  | TEGA |  |  |  |
|  | HAPMA |  |  |  |
|  | BAEDA |  |  |  |
|  | TMPETA |  |  |  |
| Length of Remaining Cured Product [mm] |  | 2.5 | 2.3 | 2.4 |

The foregoing description of the preferred embodiments of the present invention has been presented for purposes of illustration and description; however, it is not intended to be exhaustive or to limit the present invention to the precise form disclosed, and modifications and variations are possible as long as they do not deviate from the principles of the present invention.

The invention claimed is:

1. A photocurable material consisting essentially of:
   an alcohol (meth) acrylate selected from the group consisting of hydroxypropyl acrylate, dipropylene glycol diacrylate, tetraethylene glycol diacrylate, 2-hydroxy-3-acryloyloxy propyl methacrylate, and triacrylate of ethylene oxide modified trimethylolpropane;
   a photoinitiator; and
   isobornyl acrylate or stearyl methacrylate,
   wherein the photoinitiator is 1-hydroxycyclohexyl phenyl ketone or 2-hydroxy-2-methyl-1-phenylpropane-1-one.

2. The photocurable material according to claim 1, wherein the material contains 1 mass % or more of the alcohol (meth) acrylate.

3. A cured product of the photocurable material according to claim 2.

4. A material for a wiring harness, the material comprising the photocurable material according to claim 2.

5. A cured product of the photocurable material according to claim 1.

6. A material for a wiring harness, the material comprising the photocurable material according to claim 1.

7. A photocurable material consisting essentially of:
   an alcohol (meth) acrylate synthesized from (a) a monovalent alcohol having a hydroxyl group and two or more oxygen atoms in a molecule, and (b) a (meth) acrylate ingredient that is a (meth) acrylic acid or a derivative thereof, by formation of an ester bond between the hydroxyl group of the alcohol and the (meth) acrylate ingredient;
   a photoinitiator; and
   isobornyl acrylate or stearyl methacrylate,
   wherein the material contains 20 to 95% of the alcohol (meth) acrylate.

8. The photocurable material according to claim 1, wherein the material contains 20 to 95 mass % of the alcohol (meth) acrylate.

9. A method of curing, comprising:
   photocuring a (meth) acrylate monomer or oligomer in the presence of the photocurable material according to claim 1,
   wherein, during photocuring, an unreacted portion of the photoinitiator is activated by radical polymerization independent of irradiation light applied for photocuring.

* * * * *